United States Patent [19]

Kamiya et al.

[11] Patent Number: 6,020,176
[45] Date of Patent: *Feb. 1, 2000

[54] KAURENE SYNTHASE

[75] Inventors: Yuji Kamiya, Saitama; Shinjiro Yamaguchi, Tokyo, both of Japan

[73] Assignee: The Institute of Physical and Chemical Research, Saitama, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/727,308

[22] Filed: Oct. 8, 1996

[30] Foreign Application Priority Data

Oct. 9, 1995 [JP] Japan ..................... 7-261147

[51] Int. Cl.⁷ ............... C12N 9/00; C12N 1/20; C12N 15/00; C07H 21/04
[52] U.S. Cl. ............ 435/183; 435/252.3; 435/320.1; 536/23.2
[58] Field of Search ............... 435/183, 252.3, 435/320.1, 410, 468, 440; 536/23.1, 23.2

[56] References Cited

FOREIGN PATENT DOCUMENTS

WO 93/16096  8/1993  WIPO .

OTHER PUBLICATIONS

SIGMA catalog (1994), p. 52, product number A 7763.
Saito et al. (1993) Supplement to Plant Physiology 102, 349.
Saito et al. (Dec. 1995) Plant Physiol. 109, 1239–1245.
Yamaguchi et al. (1996) The Plant Journal (1996) 10, 203–213.
Duncan J. and West C., "Properties of Kaurene Synthetase from *Marah macrocarpus* Endosperm. Evidence for the Participation of Seperate but Interacting Enzymes", Plant Physiol, vol. 68, 1981, pp. 1128–1134.
Sun T and Kamiya Y, "The Arabidopsis GA1 Locus Encodes the Cyclase ent–Kaurene Synthetase A of Gibberellin Biosynthesis", The Plant Cell, vol. 6, Oct. 1994, pp. 1509–1518.

*Primary Examiner*—Ponnathapu Achutamurthy
*Assistant Examiner*—Elizabeth Slobodyansky
*Attorney, Agent, or Firm*—Wenderoth, Lind & Ponack, L.L.P.

[57] ABSTRACT

A polypeptide characterized by amino acid Nos. 1-789 of the amino acid sequence defined by SEQ ID NO:1 of the sequence listing or a polypeptide having the said amino acid sequence incorporated by insertion, deletion, or substitution of one or more amino acid residues. The peptides have catalytic activities of converting copalyl pyrophosphate to ent-kaurene and are useful for the regulation of plant growth. Also provided are DNAs encoding the polypeptides.

13 Claims, 4 Drawing Sheets

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 789 amino acids
      (B) TYPE: amino acid
      (C) STRANDEDNESS: single
      (D) TOPOLOGY: linear    (ii) MOLECULE TYPE: protein    (xi) SEQUENCE DESCRIPTION: SEQ ID NO:1:

```
Met Tyr Leu Ser Arg Pro Thr Gly Val Ala Arg Phe Ala Ala Ser
 1               5                  10                  15

Ser Ser Ser Ser Ser Ser Ala Ser Leu Phe Pro Gly Val Asp Val
                20                  25                  30

Asp Thr Thr Thr Lys Thr Gly Ala Leu His Phe Glu Glu Thr Lys
                35                  40                  45

Glu Arg Ile Lys Lys Leu Phe Asp Lys Val Glu Leu Ser Val Ser
                50                  55                  60

Ala Tyr Asp Thr Ala Trp Val Ala Met Val Pro Ser Pro Asn Ser
                65                  70                  75

Leu Asn Gln Pro Leu Phe Pro Glu Cys Ile Asn Trp Val Leu Asp
                80                  85                  90

Ser Gln His Ala Asp Gly Ser Trp Gly Leu Leu His Asn Asp Gln
                95                 100                 105

Leu Leu Met Lys Ala Asn Leu Leu Ser Thr Leu Ala Cys Val Leu
               110                 115                 120

Thr Leu Lys Arg Trp Asn Ile Gly His Asp His Met Ser Lys Ala
               125                 130                 135

Leu Asp Phe Ile Lys Ser Asn Ile Ala Ser Ala Thr Asp Glu Asn
               140                 145                 150

Gln Arg Ser Pro Val Gly Phe Asp Ile Ile Phe Pro Gly Met Ile
               155                 160                 165

Glu Tyr Ala Lys Asp Leu Asn Leu Asn Leu Pro Leu Ala Pro Thr
               170                 175                 180

Asn Val Asp Ala Leu Val Arg Lys Lys Glu Leu Glu Leu Arg Ser
               185                 190                 195

Cys Arg Ser Asn Ser Glu Gly Gly Lys Ala Tyr Leu Ala Tyr Val
               200                 205                 210

Ser Glu Gly Ile Gly Lys Leu Gln Asp Trp Asp Met Val Met Gln
               215                 220                 225

Tyr Gln Arg Lys Asn Gly Ser Leu Phe Asn Ser Pro Ser Thr Thr
               230                 235                 240

Ala Ala Ala Phe Met His Arg Asn Asp Asp Gly Cys Phe Asp Tyr
               245                 250                 255

Leu Arg Ser Leu Leu Gln Lys Phe Asp Gly Ser Val Pro Thr Ile
               260                 265                 270

Tyr Pro Leu Asp Ile Tyr Ala Arg Leu His Met Val Asp Ser Leu
               275                 280                 285

Gln Lys Phe Gly Ile Ala Arg His Phe Lys Glu Glu Ile Arg Ser
               290                 295                 300
```

-continued

```
Val Leu Asp Glu Thr Tyr Arg Cys Trp Met Gln Gly Glu Glu Asn
            305                 310                 315

Ile Phe Leu Asp Ala Ser Thr Cys Ala Met Ala Phe Arg Met Leu
            320                 325                 330

Arg Val Glu Gly Tyr Asp Val Ser Ser Asp Gln Leu Thr Gln Phe
            335                 340                 345

Ser Glu Asp Ile Phe Pro Asn Cys Leu Gly Gly Tyr Leu Lys Asp
            350                 355                 360

Phe Gly Ala Ser Leu Glu Leu Tyr Lys Ala Ser Gln Ile Ile Thr
            365                 370                 375

His Pro Asp Glu Ser Val Leu Glu Asn Ile Asn Ser Trp Thr Ser
            380                 385                 390

Arg Phe Leu Lys His Gly Leu Ser Ser Asp Ser Val Trp Ser Asp
            395                 400                 405

Arg Thr Asp Ser Val Val Lys Gln Glu Ala Val Asn Ala Leu Glu
            410                 415                 420

Phe Pro Tyr Asn Ala Thr Leu Glu Arg Leu Ile Ser Lys Arg Ala
            425                 430                 435

Met Glu Ser Tyr Ser Gly Asp Ile Val Arg Ile Ser Lys Ser Pro
            440                 445                 450

Tyr Ala Cys Leu Asn Phe Gly His Gln Asp Phe Leu Glu Leu Ala
            455                 460                 465

Val Glu Asp Phe Asn Thr Leu Gln Arg Ile His Leu Lys Glu Leu
            470                 475                 480

Glu Glu Leu Gln Arg Trp Val Val Glu Asn Lys Leu Asp Glu Leu
            485                 490                 495

Lys Phe Phe Arg Leu His Leu Gly Tyr Cys Tyr Phe Ala Ala Ala
            500                 505                 510

Ala Thr Leu Thr Asp Pro Glu Leu His Asp Ala Arg Ile Ala Trp
            515                 520                 525

Ala Gln Asn Gly Val Leu Thr Thr Val Val Asp Asp Phe Tyr Asp
            530                 535                 540

Gly Gly Gly Ser Glu Glu Leu Asp Asn Leu Ile Glu Leu Val
            545                 550                 555

Glu Lys Trp Asp Pro Asp Gly Glu Val Gly Tyr Cys Ser Lys Asp
            560                 565                 570

Val Glu Ile Val Phe Leu Ala Leu His Ser Thr Val Cys Glu Ile
            575                 580                 585

Gly Arg Arg Ala Leu Val Trp Gln Gly Arg Ser Val Met Arg Asn
            590                 595                 600

Val Ile Asp Gly Trp Leu Ala Leu Leu Lys Val Met Arg Lys Glu
            605                 610                 615

Ala Glu Trp Ser Thr Asn Lys Val Val Pro Ser Met Gly Glu Tyr
            620                 625                 630

Met Glu Gln Ala His Val Ser Phe Ala Leu Gly Pro Ile Ile Leu
            635                 640                 645

Pro Met Leu Phe Phe Val Gly Pro Lys Leu Ser Glu Glu Met Ile
            650                 655                 660

Gly Ser Cys Glu Tyr Gln Lys Leu Tyr Lys Leu Met Ser Thr Ala
            665                 670                 675

Gly Arg Leu Lys Asn Asp Ile Arg Ser Tyr Asp Arg Glu Cys Lys
            680                 685                 690
```

-continued

```
Glu Gly Lys Leu Asn Ile Leu Ser Leu Trp Met Ile Asp Gly Gly
            695                 700                 705

Gly Asn Val Thr Lys Glu Glu Ala Ile Glu Ala Ile Lys Gly Asp
            710                 715                 720

Phe Glu Arg Ala Ile Arg Glu Leu Leu Gly Leu Val Leu Gln Glu
            725                 730                 735

Asn Thr Thr Ile Pro Arg Ala Cys Lys Asp Leu Phe Trp Lys Leu
            740                 745                 750

Met Ser Ile Val Asn Leu Phe Tyr Met Glu Asp Asp Gly Tyr Thr
            755                 760                 765

Ser Asn Arg Leu Met Asn Thr Val Lys Ala Met Phe Glu Gln Pro
            770                 775                 780

Met Asp Leu Asp Ala Leu Leu Asn Lys
            785
```

(2) INFORMATION FOR SEQ ID NO:2:

(i) SEQUENCE CHARACTERISTICS:
        (A) LENGTH: 2658 base pairs
        (B) TYPE: nucleic acid
        (C) STRANDEDNESS: double
        (D) TOPOLOGY: linear     (ii) MOLECULE TYPE: cDNA     (xi) SEQUENCE DESCRIPTION: SEQ ID NO:2:

```
GAAAGCGGTA GTTTTCGGCT CTTGGCTGTT TTTGTGTACT GCCTATTCTG TTCTTTATAT      60

GCACTGAATG TGAAAATGCC TCACCAGAGT TTGATGCTGC TTCCGCAATT TCTTTGCATG     120

TCCTAAACAT ACCAGTCATG TATCTTTCCC GACCTACCGG CGTTGCCCGT TTTGCTGCCT     180

CCTCCTCCTC CTCCTCCTCA GCTTCCCTAT TCCCTGGAGT GGATGTGGAC ACAACAACTA     240

AAACTGGAGC TTTGCACTTT GAAGAAACAA AAGAAAGAAT TAAGAAATTG TTCGACAAGG     300

TTGAACTTTC AGTTTCTGCA TATGATACTG CATGGGTGGC AATGGTTCCT TCTCCAAACT     360

CTCTCAACCA ACCTCTTTTC CCCGAGTGTA TAAACTGGGT ATTAGATAGT CAACATGCTG     420

ATGGCTCATG GGGCCTACTC CACAACGATC AGTTGCTGAT GAAGGCCAAT CTCTTATCTA     480

CATTAGCATG TGTTCTTACT CTTAAGCGGT GGAATATTGG GCATGATCAT ATGAGCAAGG     540

CCCTTGATTT TATCAAGTCT AATATAGCTT CAGCTACTGA TGAGAACCAA CGTTCTCCGG     600

TGGGATTTGA CATTATTTTC CCTGGCATGA TTGAGTATGC TAAAGACTTG AATTTGAATC     660

TACCCTTGGC ACCGACGAAC GTGGATGCCT TGGTTCGAAA GAAAGAGTTG GAGCTGAGAA     720

GCTGCAGAAG CAACTCTGAA GGTGGAAAAG CCTATTTAGC GTATGTTTCA GAAGGAATTG     780

GAAAGTTACA GGACTGGGAT ATGGTCATGC AATATCAAAG GAAGAATGGA TCACTGTTTA     840

ATTCTCCATC CACTACGGCA GCGGCTTTTA TGCATAGAAA TGATGATGGC TGTTTTGATT     900

ATCTTCGCTC ACTCTTACAA AAGTTTGATG GCTCAGTTCC CACAATATAT CCTCTTGATA     960

TATATGCTCG ATTACACATG GTTGATAGCC TTCAAAAATT CGGAATTGCT CGGCATTTCA    1020

AAGAGGAGAT TAGAAGCGTA TTAGATGAAA CTTACAGGTG TTGGATGCAA GGAGAGGAAA    1080

ATATATTCTT AGATGCTTCA ACTTGTGCAA TGGCCTTTCG AATGTTACGT GTTGAAGGAT    1140

ATGATGTTTC TTCAGACCAG TTGACTCAAT TTTCAGAAGA TATCTTTCCC AATTGCCTTG    1200

GAGGATATTT AAAAGACTTC GGTGCCTCGC TGGAGTTATA TAAGGCCTCT CAGATTATCA    1260

CGCACCCCGA TGAATCTGTT CTGGAAAATA TAAACTCTTG GACTAGTCGT TTCCTGAAGC    1320

ATGGATTATC TAGTGATTCA GTTTGGTCTG ATAGAACCGA TAGTGTTGTT AAACAAGAGG    1380
```

```
CTGTTAATGC TCTTGAGTTC CCCTATAATG CAACTCTAGA ACGCCTAATA AGTAAGAGGG      1440

CAATGGAAAG TTACAGTGGA GACATTGTGA GGATTTCAAA ATCGCCATAT GCCTGCTTAA      1500

ATTTTGGCCA TCAAGATTTT CTGGAACTTG CTGTAGAGGA TTTCAATACC CTGCAACGCA      1560

TTCATCTTAA AGAACTGGAA GAGCTTCAAA GATGGGTGGT TGAAAACAAA TTGGACGAGT      1620

TGAAATTTTT CAGACTGCAC CTAGGGTACT GCTATTTTGC TGCGGCAGCG ACCCTTACTG      1680

ATCCTGAACT TCATGATGCT CGCATAGCAT GGGCACAAAA TGGTGTGCTC ACGACCGTGG      1740

TTGATGATTT CTATGATGGT GGAGGATCTG AAGAGGAATT GGATAACCTT ATAGAATTGG      1800

TGGAAAAGTG GGATCCTGAT GGGGAAGTGG GTTACTGTTC CAAGGACGTT GAGATTGTAT      1860

TTCTTGCACT GCACAGCACA GTTTGTGAAA TAGGAAGAAG AGCTTTAGTA TGGCAAGGAC      1920

GCAGTGTTAT GAGGAATGTT ATCGATGGTT GGTTGGCTCT GCTGAAGGTG ATGAGAAAGG      1980

AAGCTGAATG GTCGACAAAT AAGGTAGTGC CATCAATGGG TGAATATATG GAACAAGCCC      2040

ATGTATCATT CGCGTTGGGA CCTATAATCC TTCCAATGCT CTTCTTTGTT GGACCTAAAC      2100

TCTCAGAGGA AATGATTGGA AGCTGTGAAT ACCAGAAGTT ATATAAGCTG ATGAGCACTG      2160

CTGGTCGCCT TAAGAATGAT ATTCGATCTT ACGATAGAGA ATGCAAAGAG GGAAAGCTGA      2220

ATATTCTGTC TCTGTGGATG ATTGATGGCG GTGGTAATGT CACCAAAGAG GAGGCCATTG      2280

AAGCAATTAA AGGGGATTTT GAGAGGGCGA TAAGAGAGCT GCTGGGGTTA GTTTTGCAGG      2340

AGAACACTAC AATTCCAAGA GCTTGTAAGG ATTTGTTCTG GAAATTGATG TCCATTGTGA      2400

ATCTATTTTA CATGGAAGAT GATGGGTACA CTTCAAATAG GTTGATGAAC ACTGTAAAAG      2460

CCATGTTTGA ACAACCCATG GATCTGGATG CACTATTGAA CAAATGAACG AACAACAAAC      2520

GAAATAAGTT GTAGTGGGAA GCAGACGCCA CCTATTCACT GTCTTCTCTA CTGATCAGAT      2580

GTCTATTGCT TTCTCATTGA GGAAATGGCA AATAAAACAT TTTATGGAAA CATTTCATTG      2640

TTAAATTGAG ACAGTCTG                                                   2658

(2) INFORMATION FOR SEQ ID NO:3:

(i) SEQUENCE CHARACTERISTICS:
        (A) LENGTH:  2658 base pairs
        (B) TYPE:  nucleic acid
        (C) STRANDEDNESS:  double
        (D) TOPOLOGY:  linear (ii) MOLECULE TYPE:  cDNA (xi) SEQUENCE DESCRIPTION: SEQ ID NO:3:

GAAAGCGGTA GTTTTCGGCT CTTGGCTGTT TTTGTGTACT GCCTATTCTG TTCTTTATAT       60

GCACTGAATG TGAAAATGCC TCACCAGAGT TTGATGCTGC TTCCGCAATT TCTTTGCATG      120

TCCTAAACAT ACCAGTC                                                    137

ATG TAT CTT TCC CGA CCT ACC GGC GTT GCC CGT TTT GCT GCC TCC           182
Met Tyr Leu Ser Arg Pro Thr Gly Val Ala Arg Phe Ala Ala Ser
  1               5                  10                  15

TCC TCC TCC TCC TCC TCA GCT TCC CTA TTC CCT GGA GTG GAT GTG           227
Ser Ser Ser Ser Ser Ser Ala Ser Leu Phe Pro Gly Val Asp Val
                 20                  25                  30

GAC ACA ACA ACT AAA ACT GGA GCT TTG CAC TTT GAA GAA ACA AAA           272
Asp Thr Thr Thr Lys Thr Gly Ala Leu His Phe Glu Glu Thr Lys
                 35                  40                  45

GAA AGA ATT AAG AAA TTG TTC GAC AAG GTT GAA CTT TCA GTT TCT           317
Glu Arg Ile Lys Lys Leu Phe Asp Lys Val Glu Leu Ser Val Ser
                 50                  55                  60
```

-continued

```
GCA TAT GAT ACT GCA TGG GTG GCA ATG GTT CCT TCT CCA AAC TCT       362
Ala Thy Asp Thr Ala Trp Val Ala Met Val Pro Ser Pro Asn Ser
                65                  70                  75

CTC AAC CAA CCT CTT TTC CCC GAG TGT ATA AAC TGG GTA TTA GAT       407
Leu Asn Gln Pro Leu Phe Pro Glu Cys Ile Asn Trp Val Leu Asp
                80                  85                  90

AGT CAA CAT GCT GAT GGC TCA TGG GGC CTA CTC CAC AAC GAT CAG       452
Ser Gln His Ala Asp Gly Ser Trp Gly Leu Leu His Asn Asp Gln
                95                 100                 105

TTG CTG ATG AAG GCC AAT CTC TTA TCT ACA TTA GCA TGT GTT CTT       497
Leu Leu Met Lys Ala Asn Leu Leu Ser Thr Leu Ala Cys Val Leu
               110                 115                 120

ACT CTT AAG CGG TGG AAT ATT GGG CAT GAT CAT ATG AGC AAG GCC       542
Thr Leu Lys Arg Trp Asn Ile Gly His Asp His Met Ser Lys Ala
               125                 130                 135

CTT GAT TTT ATC AAG TCT AAT ATA GCT TCA GCT ACT GAT GAG AAC       587
Leu Asp Phe Ile Lys Ser Asn Ile Ala Ser Ala Thr Asp Glu Asn
               140                 145                 150

CAA CGT TCT CCG GTG GGA TTT GAC ATT ATT TTC CCT GGC ATG ATT       632
Gln Arg Ser Pro Val Gly Phe Asp Ile Ile Phe Pro Gly Met Ile
               155                 160                 165

GAG TAT GCT AAA GAC TTG AAT TTG AAT CTA CCC TTG GCA CCG ACG       677
Glu Tyr Ala Lys Asp Leu Asn Leu Asn Leu Pro Leu Ala Pro Thr
               170                 175                 180

AAC GTG GAT GCC TTG GTT CGA AAG AAA GAG TTG GAG CTG AGA AGC       722
Asn Val Asp Ala Leu Val Arg Lys Lys Glu Leu Glu Leu Arg Ser
               185                 190                 195

TGC AGA AGC AAC TCT GAA GGT GGA AAA GCC TAT TTA GCG TAT GTT       767
Cys Arg Ser Asn Ser Glu Gly Gly Lys Ala Tyr Leu Ala Tyr Val
               200                 205                 210

TCA GAA GGA ATT GGA AAG TTA CAG GAC TGG GAT ATG GTC ATG CAA       812
Ser Glu Gly Ile Gly Lys Leu Gln Asp Trp Asp Met Val Met Gln
               215                 220                 225

TAT CAA AGG AAG AAT GGA TCA CTG TTT AAT TCT CCA TCC ACT ACG       857
Tyr Gln Arg Lys Asn Gly Ser Leu Phe Asn Ser Pro Ser Thr Thr
               230                 235                 240

GCA GCG GCT TTT ATG CAT AGA AAT GAT GAT GGC TGT TTT GAT TAT       902
Ala Ala Ala Phe Met His Arg Asn Asp Asp Gly Cys Phe Asp Tyr
               245                 250                 255

CTT CGC TCA CTC TTA CAA AAG TTT GAT GGC TCA GTT CCC ACA ATA       947
Leu Arg Ser Leu Leu Gln Lys Phe Asp Gly Ser Val Pro Thr Ile
               260                 265                 270

TAT CCT CTT GAT ATA TAT GCT CGA TTA CAC ATG GTT GAT AGC CTT       992
Tyr Pro Leu Asp Ile Tyr Ala Arg Leu His Met Val Asp Ser Leu
               275                 280                 285

CAA AAA TTC GGA ATT GCT CGG CAT TTC AAA GAG GAG ATT AGA AGC      1037
Gln Lys Phe Gly Ile Ala Arg His Phe Lys Glu Glu Ile Arg Ser
               290                 295                 300

GTA TTA GAT GAA ACT TAC AGG TGT TGG ATG CAA GGA GAG GAA AAT      1082
Val Leu Asp Glu Thr Tyr Arg Cys Trp Met Gln Gly Glu Glu Asn
               305                 310                 315

ATA TTC TTA GAT GCT TCA ACT TGT GCA ATG GCC TTT CGA ATG TTA      1127
Ile Phe Leu Asp Ala Ser Thr Cys Ala Met Ala Phe Arg Met Leu
               320                 325                 330

CGT GTT GAA GGA TAT GAT GTT TCT TCA GAC CAG TTG ACT CAA TTT      1172
Arg Val Glu Gly Tyr Asp Val Ser Ser Asp Gln Leu Thr Gln Phe
               335                 340                 345

TCA GAA GAT ATC TTT CCC AAT TGC CTT GGA GGA TAT TTA AAA GAC      1217
Ser Glu Asp Ile Phe Pro Asn Cys Leu Gly Gly Tyr Leu Lys Asp
```

-continued

|   |   |   |   |   |   |   |   |   |   |   |   |   |   |   |
|---|---|---|---|---|---|---|---|---|---|---|---|---|---|---|
|   |   |   | 350 |   |   |   | 355 |   |   |   | 360 |   |   |   |

```
TTC GGT GCC TCG CTG GAG TTA TAT AAG GCC TCT CAG ATT ATC ACG       1262
Phe Gly Ala Ser Leu Glu Leu Tyr Lys Ala Ser Gln Ile Ile Thr
            365                 370                 375

CAC CCC GAT GAA TCT GTT CTG GAA AAT ATA AAC TCT TGG ACT AGT       1307
His Pro Asp Glu Ser Val Leu Glu Asn Ile Asn Ser Trp Thr Ser
            380                 385                 390

CGT TTC CTG AAG CAT GGA TTA TCT AGT GAT TCA GTT TGG TCT GAT       1352
Arg Phe Leu Lys His Gly Leu Ser Ser Asp Ser Val Trp Ser Asp
            395                 400                 405

AGA ACC GAT AGT GTT GTT AAA CAA GAG GCT GTT AAT GCT CTT GAG       1397
Arg Thr Asp Ser Val Val Lys Gln Glu Ala Val Asn Ala Leu Glu
            410                 415                 420

TTC CCC TAT AAT GCA ACT CTA GAA CGC CTA ATA AGT AAG AGG GCA       1442
Phe Pro Tyr Asn Ala Thr Leu Glu Arg Leu Ile Ser Lys Arg Ala
            425                 430                 435

ATG GAA AGT TAC AGT GGA GAC ATT GTG AGG ATT TCA AAA TCG CCA       1487
Met Glu Ser Tyr Ser Gly Asp Ile Val Arg Ile Ser Lys Ser Pro
            440                 445                 450

TAT GCC TGC TTA AAT TTT GGC CAT CAA GAT TTT CTG GAA CTT GCT       1532
Tyr Ala Cys Leu Asn Phe Gly His Gln Asp Phe Leu Glu Leu Ala
            455                 460                 465

GTA GAG GAT TTC AAT ACC CTG CAA CGC ATT CAT CTT AAA GAA CTG       1577
Val Glu Asp Phe Asn Thr Leu Gln Arg Ile His Leu Lys Glu Leu
            470                 475                 480

GAA GAG CTT CAA AGA TGG GTG GTT GAA AAC AAA TTG GAC GAG TTG       1622
Glu Glu Leu Gln Arg Trp Val Val Glu Asn Lys Leu Asp Glu Leu
            485                 490                 495

AAA TTT TTC AGA CTG CAC CTA GGG TAC TGC TAT TTT GCT GCG GCA       1667
Lys Phe Phe Arg Leu His Leu Gly Tyr Cys Tyr Phe Ala Ala Ala
            500                 505                 510

GCG ACC CTT ACT GAT CCT GAA CTT CAT GAT GCT CGC ATA GCA TGG       1712
Ala Thr Leu Thr Asp Pro Glu Leu His Asp Ala Arg Ile Ala Trp
            515                 520                 525

GCA CAA AAT GGT GTG CTC ACG ACC GTG GTT GAT GAT TTC TAT GAT       1757
Ala Gln Asn Gly Val Leu Thr Thr Val Val Asp Asp Phe Tyr Asp
            530                 535                 540

GGT GGA GGA TCT GAA GAG GAA TTG GAT AAC CTT ATA GAA TTG GTG       1802
Gly Gly Gly Ser Glu Glu Glu Leu Asp Asn Leu Ile Glu Leu Val
            545                 550                 555

GAA AAG TGG GAT CCT GAT GGG GAA GTG GGT TAC TGT TCC AAG GAC       1847
Glu Lys Trp Asp Pro Asp Gly Glu Val Gly Tyr Cys Ser Lys Asp
            560                 565                 570

GTT GAG ATT GTA TTT CTT GCA CTG CAC AGC ACA GTT TGT GAA ATA       1892
Val Glu Ile Val Phe Leu Ala Leu His Ser Thr Val Cys Glu Ile
            575                 580                 585

GGA AGA AGA GCT TTA GTA TGG CAA GGA CGC AGT GTT ATG AGG AAT       1937
Gly Arg Arg Ala Leu Val Trp Gln Gly Arg Ser Val Met Arg Asn
            590                 595                 600

GTT ATC GAT GGT TGG TTG GCT CTG CTG AAG GTG ATG AGA AAG GAA       1982
Val Ile Asp Gly Trp Leu Ala Leu Leu Lys Val Met Arg Lys Glu
            605                 610                 615

GCT GAA TGG TCG ACA AAT AAG GTA GTG CCA TCA ATG GGT GAA TAT       2027
Ala Glu Trp Ser Thr Asn Lys Val Val Pro Ser Met Gly Glu Tyr
            620                 625                 630

ATG GAA CAA GCC CAT GTA TCA TTC GCG TTG GGA CCT ATA ATC CTT       2072
Met Glu Gln Ala His Val Ser Phe Ala Leu Gly Pro Ile Ile Leu
            635                 640                 645

CCA ATG CTC TTC TTT GTT GGA CCT AAA CTC TCA GAG GAA ATG ATT       2117
```

```
Pro Met Leu Phe Phe Val Gly Pro Lys Leu Ser Glu Glu Met Ile
            650                 655                 660
GGA AGC TGT GAA TAC CAG AAG TTA TAT AAG CTG ATG AGC ACT GCT        2162
Gly Ser Cys Glu Tyr Gln Lys Leu Tyr Lys Leu Met Ser Thr Ala
            665                 670                 675
GGT CGC CTT AAG AAT GAT ATT CGA TCT TAC GAT AGA GAA TGC AAA        2207
Gly Arg Leu Lys Asn Asp Ile Arg Ser Tyr Asp Arg Glu Cys Lys
            680                 685                 690
GAG GGA AAG CTG AAT ATT CTG TCT CTG TGG ATG ATT GAT GGC GGT        2252
Glu Gly Lys Leu Asn Ile Leu Ser Leu Trp Met Ile Asp Gly Gly
            695                 700                 705
GGT AAT GTC ACC AAA GAG GAG GCC ATT GAA GCA ATT AAA GGG GAT        2297
Gly Asn Val Thr Lys Glu Glu Ala Ile Glu Ala Ile Lys Gly Asp
            710                 715                 720
TTT GAG AGG GCG ATA AGA GAG CTG CTG GGG TTA GTT TTG CAG GAG        2342
Phe Glu Arg Ala Ile Arg Glu Leu Leu Gly Leu Val Leu Gln Glu
            725                 730                 735
AAC ACT ACA ATT CCA AGA GCT TGT AAG GAT TTG TTC TGG AAA TTG        2387
Asn Thr Thr Ile Pro Arg Ala Cys Lys Asp Leu Phe Trp Lys Leu
            740                 745                 750
ATG TCC ATT GTG AAT CTA TTT TAC ATG GAA GAT GAT GGG TAC ACT        2432
Met Ser Ile Val Asn Leu Phe Tyr Met Glu Asp Asp Gly Tyr Thr
            755                 760                 765
TCA AAT AGG TTG ATG AAC ACT GTA AAA GCC ATG TTT GAA CAA CCC        2477
Ser Asn Arg Leu Met Asn Thr Val Lys Ala Met Phe Glu Gln Pro
            770                 775                 780
ATG GAT CTG GAT GCA CTA TTG AAC AAA TGA                            2507
Met Asp Leu Asp Ala Leu Leu Asn Lys
            785

ACGAACAACA AACGAAATAA GTTGTAGTGG GAAGCAGACG CCACCTATTC ACTGTCTTCT  2567

CTACTGATCA GATGTCTATT GCTTTCTCAT TGAGGAAATG GCAAATAAAA CATTTTATGG  2627

AAACATTTCA TTGTTAAATT GAGACAGTCT G                                 2658

(2) INFORMATION FOR SEQ ID NO:4:

(i) SEQUENCE CHARACTERISTICS:
        (A) LENGTH:  20 amino acids
        (B) TYPE:  amino acid
        (C) STRANDEDNESS:  single
        (D) TOPOLOGY:  linear (ii) MOLECULE TYPE:  protein (xi) SEQUENCE DESCRIPTION: SEQ ID NO:4:

Ala Ser Gln Ile Ile Thr His Pro Asp Glu Ser Val Leu Glu Asn
  1               5                  10                  15

Ile Asn Ser Trp Thr
                 20

(2) INFORMATION FOR SEQ ID NO:5:

(i) SEQUENCE CHARACTERISTICS:
        (A) LENGTH:  8 amino acids
        (B) TYPE:  amino acid
        (C) STRANDEDNESS:  single
        (D) TOPOLOGY:  linear (ii) MOLECULE TYPE:  protein (xi) SEQUENCE DESCRIPTION: SEQ ID NO:5:

Glu Ala Glu Trp Ser Thr Asn Lys
  1               5
```

(2) INFORMATION FOR SEQ ID NO:6:

(i) SEQUENCE CHARACTERISTICS:
        (A) LENGTH:  15 amino acids
        (B) TYPE:  amino acid
        (C) STRANDEDNESS:  single
        (D) TOPOLOGY:  linear (ii) MOLECULE TYPE:  protein (xi) SEQUENCE DESCRIPTION: SEQ ID NO:6:

Arg Ala Met Glu Ser Tyr Ser Gly Asp Ile Val Arg Ile Ser Lys
 1               5                  10                  15

(2) INFORMATION FOR SEQ ID NO:7:

(i) SEQUENCE CHARACTERISTICS:
        (A) LENGTH:  9 amino acids
        (B) TYPE:  amino acid
        (C) STRANDEDNESS:  single
        (D) TOPOLOGY:  linear (ii) MOLECULE TYPE:  protein (xi) SEQUENCE DESCRIPTION: SEQ ID NO:7:

His Gly Leu Ser Ser Asp Ser Val Trp
 1               5

(2) INFORMATION FOR SEQ ID NO:8:

(i) SEQUENCE CHARACTERISTICS:
        (A) LENGTH:  13 amino acids
        (B) TYPE:  amino acid
        (C) STRANDEDNESS:  single
        (D) TOPOLOGY:  linear (ii) MOLECULE TYPE:  protein (xi) SEQUENCE DESCRIPTION: SEQ ID NO:8:

Leu Gln Asp Trp Ser Met Val Met Gln Tyr Gln Arg Lys
 1               5                  10

(2) INFORMATION FOR SEQ ID NO:9:

(i) SEQUENCE CHARACTERISTICS:
        (A) LENGTH:  13 amino acids
        (B) TYPE:  amino acid
        (C) STRANDEDNESS:  single
        (D) TOPOLOGY:  linear (ii) MOLECULE TYPE:  protein (xi) SEQUENCE DESCRIPTION: SEQ ID NO:9:

Leu Gln Asp Trp Asp Met Val Met Gln Tyr Gln Arg Lys
 1               5                  10

KAURENE SYNTHASE

BACKGROUND OF THE INVENTION

1. Field of the Invention

The present invention relates to a novel kaurene synthase and a DNA which encodes the enzyme.

2. Description of the Related Art ent-Kaurene is an important intermediate in gibberellin (GA) biosynthesis, and is synthesized from geranylgeranyl pyrophosphate (GGPP) via copalyl pyrophosphate (CPP). These steps are catalyzed by ent-kaurene synthase A (KSA) and ent-kaurene synthase B (KSB), respectively (Coolbaugh, R. C., The Biochemistry and Physiology of Gibberellins, Vol.1, Pracger Publishers, New York, pp.53–98, 1983). Other terpenoids such as carotenoids, xanthophyll, and phytol are also synthesized from geranylgeranyl pyrophosphate as a precursor, while copalyl pyrophosphate is used as precursors for macrocyclic diterpene biosyntheses. ent-kaurene synthase A and ent-kaurene synthase B are thus important enzymes in the initial stage of gibberellin biosynthesis (Coolbaugh, supra; Chung C. H. et al., Plant Physiol., 80, pp.544–548, 1986; Graebe, J. E., Annu. Rev. Plant. Physiol., 38, pp.419–465, 1987).

Duncan et al. separated ent-kaurene synthase A and ent-kaurene synthase B from native cucumber (Marah macrocarpus L.) using a QAE column. The authors suggested that the conversion of geranylgeranyl pyrophosphate to ent-kaurene is catalyzed by the two distinguishable enzymes (Duncan, J. D. and West C. A., Plant Physiol., 68, pp.1128–1134, 1981). In this article, it is shown that ent-kaurene synthase A and ent-kaurene synthase B closely associated with each other during the ent-kaurene synthesis and that ent-kaurene synthase B preferentially utilized endogenous copalyl pyrophosphate produced by ent-kaurene synthase A rather than exogenous copalyl pyrophosphate.

As shown in the scheme set out below, ent-kaurene synthase A catalyzes the conversion of geranylgeranyl pyrophosphate (GGPP) to copalyl pyrophosphate (CPP), and the resulting copalyl pyrophosphate is successively converted to ent-kaurene by ent-kaurene synthase B.

ent-Kaurene

In recent years, cDNA clonings of gibberellin biosynthases have been reported. GA1 locus of Arabidopsis was isolated by genomic subtraction (Sun, T. P., et al., Plant Cell, 4, pp.119–128, 1992) and the corresponding cDNA clone was verified to encode ent-kaurene synthase A by overexpression system in E. coli (Sun T. P. and Kamiya, Y., Plant Cell, 6, pp.1509–1518, 1994). An1 locus of maize was cloned by the transposon tagging technique and the deduced amino acid sequence from the cDNA was revealed to have significant homology with Arabidopsis ent-kaurene synthase A, although the function of the expressed protein remains unknown (Bensen, R. J., et al., Plant Cell, 7, pp.75–84, 1995). A putative 3b-hydroxylase in gibberellin biosynthesis was also cloned by the T-DNA tagging method using Arabidopsis GA4 mutant (Chiang, H.-h., et al., Plant Cell, 7, pp.195–201, 1995).

As for ent-kaurene synthase B, the enzyme was partially purified from Ricinus communis (Spickett, C. M., et al., Phytochem., 37, pp.971–973, 1994). Ricinus communis biosynthesizes kaurene and its family diterpenes, i.e., bayarene, torakiroban, and sandarakopymaradiene. These compounds are synthesized through selective cyclizations from a common intermediate, copalyl pyrophosphate. Although a cloning of an ent-kaurene synthase B gene was attempted (15th International Conference on Plant Growth Substance, Jul. 14–18, 1995, Minneapolis, USA, Kamiya, Y., et al., Subject No. 040 and Saito, T., et al., Subject No. 110), the complete sequence of a cDNA and the amino acid sequence of the enzyme has not been reported.

SUMMARY OF THE INVENTION

An object of the present invention is to provide a purified ent-kaurene synthase B. Another object of the present invention is to provide the amino acid sequence of the enzyme and a DNA encoding the enzyme.

The present inventors succeeded in purifying an ent-kaurene synthase B from endosperm of pumpkin (Cucurbita maxima L.) seeds. The inventors revealed its amino acid sequence (a partial sequence), and based on the information of the amino acid sequence, they succeeded in cloning a gene which encodes ent-kaurene synthase B.

Accordingly, the present invention provides a polypeptide which is characterized by the amino acid sequence as defined by SEQ ID NO:1 of the sequence listing (amino acids No. 1–789: the amino acid sequence is shown by the JUPAC three-letter symbols). The polypeptide can act as an enzyme having the catalytic activity of converting copalyl pyrophosphate to ent-kaurene (in the specification, this enzyme will be occasionally referred to as ent-kaurene synthase B, or more symply as KSB). According to another embodiment of the present invention, DNAs encoding the above-described polypeptide are provided. As a preferred embodiment thereof, a DNA which is characterized by nucleotide Nos. 138–2507 (including the termination codon) of the nucleic acid sequence as defined by SEQ ID NO:2 of the sequence listing is also provided.

DETAILED DESCRIPTION OF THE INVENTION

In addition to the aforementioned naturally derived ent-kaurene synthase B from pumpkin, any polypeptides also fall within the scope of the polypeptides provided by the present invention which have the amino acid sequence defined by SEQ ID NO:1 of the sequence listing together with insertion, deletion, and/or substitution by one or more amino acid residues and which have the catalytic activity of converting copalyl pyrophosphate to ent-kaurenethe. Particularly preferred embodiments of the polypeptide of the present invention include naturally-derived ent-kaurene synthases expressed in plant bodies such as pumpkin, maize, rice, or soybean.

Detailed descriptions will be given in the examples of the specification as for the evaluation of the enzymatic function of the naturally-derived ent-kaurene synthase B from pumpkin, which is a preferred embodiment of the polypeptide of the present invention. Accordingly, it can be readily understood that an ordinarily skilled artisan can easily determine whether or not a variant polypeptide, having insertion, deletion, and/or substitution of one or more constituent amino acid residues of the amino acid sequence of said enzyme, has the desired activity.

According to another embodiment of the present invention, polypeptides are provided which contain in their molecules amino acid sequences of the polypeptide of the naturally-derived ent-kaurene synthase B from pumpkin or variant polypeptides thereof and which have catalytic activities of converting copalyl pyrophosphate to ent-kaurene. These polypeptides are characterized by the entire sequences of the above-described polypeptides contained as a part thereof.

According to further embodiments of the present invention, polypeptides having catalytic activities of converting copalyl pyrophosphate to ent-kaurene are also provided which consist of, or alternatively comprise as a part thereof, a partial amino acid sequence of the polypeptide of the naturally-derived ent-kaurene synthase B from pumpkin or its variant polypeptide wherein said partial sequence has the catalytic activity of converting copalyl pyrophosphate to ent-kaurene, i.e., being a so-called active domain. Such peptides may consist solely of the active domain, per se, or may comprise the active domain as a part thereof.

For example, the naturally-derived ent-kaurene synthase B obtained from pumpkin, which is a preferred embodiment of the present invention, may occasionally be retained inside the cells after expression. A membrane-binding domain (a hydrophobic domain) may be selectively removed from the entire amino acid sequence of the enzyme and the remaining polypeptide containing an active domain can be ligated to a signal peptide to produce an extracellularly releasable soluble enzyme. For the determination of the hydrophobic domain, methods well known in the art, e.g., the method of Kyte et al. (Kyte, J. et al., J. Mol. Bio., 157, pp.105–132, 1982), the Hopp & Woods method and the like can be employed.

According to further embodiments of the present invention, DNAs which encode any one of the above-described polypeptides are provided. For example, the present invention encompasses DNAs encoding the aforementioned naturally-derived ent-kaurene synthase B from pumpkin, and as a preferred example, the DNA characterized by nucleotides of from No. 138 to 2507 (including the termination codon) of the nucleic acid sequence as defined by SEQ ID NO:3 of the sequence listing.

Furthermore, examples of DNAs that fall within the scope of the present invention include DNAs which encode a variant polypeptide having the catalytic activity of converting copalyl pyrophosphate to ent-kaurene wherein said polypeptide includes insertion, deletion, and/or substitution of one or more of the constituent amino acid residues of the amino acid sequence of the naturally-derived ent-kaurene synthase B from pumpkin; and DNAs which encode a polypeptide having the catalytic activity of converting copalyl pyrophosphate to ent-kaurene wherein said DNA has a DNA sequence characterized by the nucleic acids of from 138 to 2507 (including termination codon) of the nucleic acid sequence as defined by SEQ ID NO:3 of the sequence listing in which one or more of the constituent nucleotides are inserted, deleted, and/or substituted.

DNAs which act as antisense DNAs against the gene containing the aforementioned sense DNAs also fall within the scope of the present invention. One example of such antisense DNAs is a DNA which acts as an antisense DNA against an ent-kaurene synthase B gene comprising a DNA encoding any one of the aforementioned polypeptides wherein said DNA sequence includes insertion, deletion, or substitution of one or more of the constituting nucleotides of the sequence that is complimentary to the DNA characterized by nucleotides of from No. 138 to 2507 (including the termination codon) of the nucleic acid sequence defined as SEQ ID NO:3 of the sequence listing.

As for the DNA encoding the naturally-derived ent-kaurene synthase B from pumpkin, a preferred example of the DNAs of the present invention and method for the isolation thereof will be detailed in the examples of the specification. Therefore, DNAs encoding ent-kaurene synthase Bs derived from pumpkin and other plants can be readily obtained by those skilled in the art by following the methods described in the examples, or alternatively, by referring to the description and optionally applying appropriate modifications or alterations to the described methods. Furthermore, it should be understood that DNAs containing any one of the aforementioned DNAs as a part thereof also fall within the scope of the present invention.

The DNAs of the present invention and antisense DNAs against said DNAs are useful for the regulation of the expression of ent-kaurene synthase B in plant that has important functions in the growths of plants and seeds. For example, a transgenic plant introduced with the DNA of the present invention may have an increased height, and its promoted growth can be expected. A transgenic plant introduced with the antisense DNA may have a reduced height while the quantities of seeds and fruits can be maintained. Therefore, a plant bearable against a damage from a storm and flood can be obtained.

The present invention also provides a recombinant vector containing the aforementioned DNA and a transformant cell containing the recombinant vector. Although the types of the vectors are not particularly limited so long as available to those skilled in the art, an appropriate vector should be chosen depending on a combination with a host cell to be transformed. Types of host cell are also not particularly limited and any cells such as microbial cells (prokaryote), e.g., E. coli and animal or plant cells (eukaryote) can be used.

EXAMPLES

The present invention will be more specifically explained by referring to the examples. However, the scope of the present invention is not limited to the examples set out below.

Example 1

Purification of the ent-kaurene synthase B (KSB)

(1) Materials and Methods
(A) Plant Materials and Chemicals

Seeds of pumpkin (Cucurbita maxima L.) cv. "Riesenmelone gelb vernetzt" were obtained from van Waveren Pflanzenzucht, Rosdorf, Germany through Professor Jan Graebe. Plants were cultivated in a field in Saitama, Japan, and immature fruits were harvested between the middle of June and early July in 1992, when the cotyledons had reached about half their final length.

Geranylgeraniol was a gift from Dr. T. Takigawa of Kurare Co. Ltd. (Kurashiki, Japan). Copalic acid (Nakano, T. and Djerassi C., J. Org. Chem., 26, pp.167–173, 1961) and natural resin "Brazil copal" (which contains copalic acid) were gifts from Prof. T. Nakano of Venezuela National Institute of Science (Caracas, Venezuela) and Prof. Y. Ichinohe and Dr. H. Sakamaki of Nihon University, respectively. [$^3$H]Sodium borohydride (296 GBq mmol$^{-1}$) was purchased from Amersham Int. (Buckinghamshire, UK). [1-$^3$H] geranylgeraniol (74 GBq mmol$^{-1}$) and [15-$^3$H]copalol (74 GBq mmol$^{-1}$) were prepared by reduction of geranylgeranial and copalal with [$^3$H]sodium borohydride (Bensen, R. J. and Zeevaart, J. A., J. Plant Growth Regul., 9, pp.237–242, 1990).

Tritium labeled geranylgeranyl pyrophosphate (GGPP) and copalyl pyrophosphate (CPP) were prepared through chlorination and subsequent pyrophosphorylation (Davisson et al., J. Org. Chem., 51, pp.4768–4779, 1986). The pyrophosphates were purified by reverse-phase chromatography on a Bond-Elut C18 cartridge (1 mL, Varian, Harbor City, Calif.) with stepwise elution using 20, 30, 50 and 70% (v/v) aqueous methanol. Optically pure uniconazole (Izumi, K., et al., Plant Cell Physiol., 26, pp.821–827, 1985) was obtained from Sumitomo Chemical Co.
(B) Enzyme Assay and Protein Assay KSB activity was measured in the incubation mixtures consisted of enzyme solution in Kpi buffer (50 mM, pH 8.0, 100 μL) containing glycerol (10%, v/v), dithiothreitol (DTT) (2 mM), MgCl$_2$ (5 mM), uniconazole (20 μM, Izumi, K., et al., Plant Cell Physiol., 26, pp.821–827, 1985) and [15-$^3$H]CPP (1.0 kBq). [1-$^3$H]GGPP (1.0 kBC) was used as a substrate for the measurement of KSAB activity (conversion from geranylgeranyl pyrophosphate (GGPP) to ent-kaurene).

The mixture was incubated at 30° C. for 30 min, and the enzyme reaction was terminated by the addition of acetone (200 μL) and water (100 μL). The mixture was extracted with n-hexane (400 μL), and 300 μL alibuots of the extract were concentrated in vacuo and applied to a silica gel plate. After developing with n-hexane, the radioactivity of the silica gel of the ent-kaurene region (Rf 0.6–1.0) was determined. One unit of kaurene synthase activity was defined as the production of 1 pmol of ent-kaurene per minute. The protein concentration was determined using BIO-RAD (Richmond, Calif.) microassay (Bradford, M. M., Anal. Biochem., 72, pp.248–245, 1976) using BSA as the standard.
(C) Purification of KSB All procedures were performed at 0 to 40° C. The following buffers were used: buffer A, 50 mM kPi buffer (pH 8.0) containing 2 mM DTT; buffer B, buffer A containing 10% glycerol; buffer C, 20 mM Tris-HCl buffer (pH 7.4) containing 10% glycerol and 2 mM DTT; buffer D, 1 mM KPi buffer (pH 6.0) containing 20% glycerol, 2 mM DTT and 5 MM MgCl$_2$.

Crude enzyme extract (1 L) was prepared by th e method of Graebe et al. (Graebe, J. E., et al., Pytochem., 13, pp.1433–1440, 1974). Butyl-Toyopearl 650S gel (Toso, Tokyo, Japan) was packed into a glass column (AP-1, 10 mm×100 mm, Waters, Millipore Corp., Milford, Mass.) and the column was equilibrated with a buffer A containing 1.7 M (NH$_4$)$_2$SO$_4$. Ammonium sulfate was added to the crude enzyme preparation (77 mL) to 1.7 M of a final concentration, and stirred for 10 min. The enzyme solution was centrifuged at 2,000 g for 10 min, and the supernatant was loaded onto the column at a flow rate of 3.0 mL/min. The column was eluted with a 30-min linear gradient of 1.7 to 0 M (NH$_4$)$_2$SO$_4$, and then with buffer B for 45 min. The fraction volume was 6 mL and a 5 μL aliquot of each fraction was assayed.

The major active fractions (No. 32–37) were concentrated by ultrafiltration (YM-10 filter, Amicon, Beverly, Mass.) and the active fractions from several runs were pooled (53 mL). The butyl-purified enzyme preparation equilibrated with buffer C (8.4 mL) was loaded onto a DEAE-8HR column (10 mm×100 mm, Waters). The column was eluted with a 50-min linear gradient of 0 to 500 mM NaCl in buffer C. The flow rate was 1.0 mL/min and the fraction volume was 2.0 mL.

The active fractions (No. 33–38) were pooled and concentrated by ultrafiltration (YM-10). Ammonium sulfate was added to the DEAE-purified enzyme preparation (7.9 mL) to 1.7 M of a final concentration. The enzyme solution was loaded onto a TSK phenyl-5PW column (7.5 mm×75 mm, Toso), which was equilibrated with buffer B containing 1.7 M (NH$_4$)$_2$SO$_4$. The column was eluted with a 60-min linear gradient of 1.7 to 0 M (NH$_4$)$_2$SO$_4$, and then with buffer B for 30 min. The flow rate was 1.0 mL/min and 2.0 mL fractions were collected. The major KSB activity was found in fractions No. 37–41. For the second DEAE ion exchange chromatography, the phenyl-purified enzyme preparation (2.0 mL) was charged to the DEAE column and eluted as described above.

The fractions containing most of the KSB activity (No. 36–38) were concentrated to 300 μL by ultrafiltration (Centicon 30, Amicon). This preparation was charged to a hydroxyapatite column (TONEN TAPS-050805 HG, 8.0 mm×50 mm, Tonen, Tokyo, Japan) equilibrated with buffer D. The column was eluted with a 60-min linear gradient of 1 to 500 mM phosphate. The flow rate was 1.0 mL/min and the fraction volume was 1 mL. The major KSB active fractions (No. 23–25) were concentrated by ultrafiltration (Centricon 30) and stored at −80° C. (70 μg, 673 units).
(D) Gel Permeation Chromatography The phenyl-purified enzyme preparation was charged onto the gel permeation column (TSK G3000SWx1, 7.8 mm×300 mm, Toso, Tokyo, Japan) which was pre-equilibrated with buffer B containing 200 mM NaCl. The column was eluted with the same buffer at a flow rate of 0.4 mL/min and fractions were collected every 30 sec.

(E) SDS-PAGE

Active enzyme fractions of the sequential purification steps were analyzed by SDS-PAGE using a 7.5% (w/v) gel (Laemmli, U.K., Nature, 227, pp.680–685, 1970). Approximately 3 µg of total protein was applied to each lane. After electrophoresis, proteins were visualized by Coomassie Brilliant Blue R250 (CBB) staining. Ovalbumin (45.0 kD), BSA (66.2 kD), phosphorylase B (97.4 kD), B-galactosidase (116 kD), and myosin (200 kD) were used as standard proteins (BIO-RAD).

(F) Properties of KSB

When the properties of KSB were examined, the phenyl-purified enzyme preparation (0.47 µg of total protein) was used as the enzyme solution. The amount of [1-$^3$H]CPP was 2.2 kBq and the incubation period was 15 min. The other conditions were the same as those for the enzyme assay. To determine the optimal pH, KPi buffer (50 mM) adjusted to a particular pH (pH 4.5 to 9.0) was used. To determine the $K_m$ value, the phenyl-purified enzyme preparation (1.2 µg of total protein) was used, and the concentrations of [1-$^3$H]CPP were in the range of 7 to 480 nM. The production of ent-kaurene was calculated and the $K_m$ value was determined from a Lineweaver-Burk plot.

(G) N-terminal Amino-acid and Internal Peptide Sequence Analysis

The final purified enzyme preparation (14.5 µg) was purified on a 7.5% (w/v) polyacrylamide gel. Proteins were electroblotted to a polyvinylidene difluoride membrane and visualized (Matsudaira, P., J. Biol. Chem., 262, pp.10035–10038, 1987). The 81 kD band on the membrane was cut out and the amino-acid sequence of the protein was analyzed by a protein sequencer (477A protein sequencer, Applied Biosystems Inc., Foster City, Calif.).

For internal peptide sequence analysis, the 81 kD protein was digested in situ (Kawasaki, H., et al., Anal. Biochem., 191, pp.332–336, 1990) with the Acromobacter protease I (a gift from Dr. T. Masaki of Ibaraki University). The generated peptide fragments were extracted from the gel and separated by reverse phase HPLC using a Superspher RP-Select B column. Aqueous 0.09% (v/v) TFA and 80% (v/v) acetonitrile containing 0.075% (v/v) TFA were used as eluents A and B, respectively. The flow rate was 0.2 mL/min and a 32-min linear gradient of 0 to 80% of eluent B was used (1090M HPLC system, Hewlett Packard, Avondale, Pa.). Absorbances at 215, 254, 275 and 290 nm were monitored. Amino acid sequences of separated peptides were analyzed with the protein sequencer.

(H) Polyclonal Antibodies for the 81 kD Protein

A major peptide fragment of 81 kD protein, ASQIITHP-DESVLENINSW T (shown in the single character code and Ala-Ser-Gln-Ile-Ile-Thr-His-Pro-Asp-Glu-Ser-Val-Leu-Glu-Asn-Ile-Asn-Ser-Trp-Thr shown in three-letter code as SEQ ID No. 4), was custom synthesized by Quality Controlled Biochemicals Inc. (Hopkinton, Mass.). The synthetic peptide (3.1 mg, 1.4 nmol) was combined to keyhole limpet hemocyanin by using an Imjet Immunogen EDC Conjugation Kit (Pierce, Rockford, Ill.) according to the manufacturer's instructions. The combined protein (1 mg) was injected into a rabbit three times at intervals of 2 weeks, and 4 weeks after the last injection antiserum was collected by centrifugation of the blood. Immunogloblin G was purified from the antiserum using a HiTrap Protein G column (1 mL, Pharmacia LKB biotechnology, Uppsala, Sweden). About 10 µL of each fraction of the 2nd DEAE-chromatography was resolved on two 7.5% SDS-PAGE gels. One of the gels was stained with CBB solution, and proteins on the other gel were electroblotted onto a nitrocellulose membrane. The nitrocellulose membrane was treated with the IgG at room temperature for 2 hr and then with alkaline phosphatase conjugated anti-rabbit-IgG at the same temperature for another 2 hr. The membrane was treated with nitro-blue tetrazolium chloride and 5-bromo-4-chloro-3'-indolyl-phosphate (Pierce) to visualize proteins.

(2) Results (A) Purification of KSB

Figure 1:
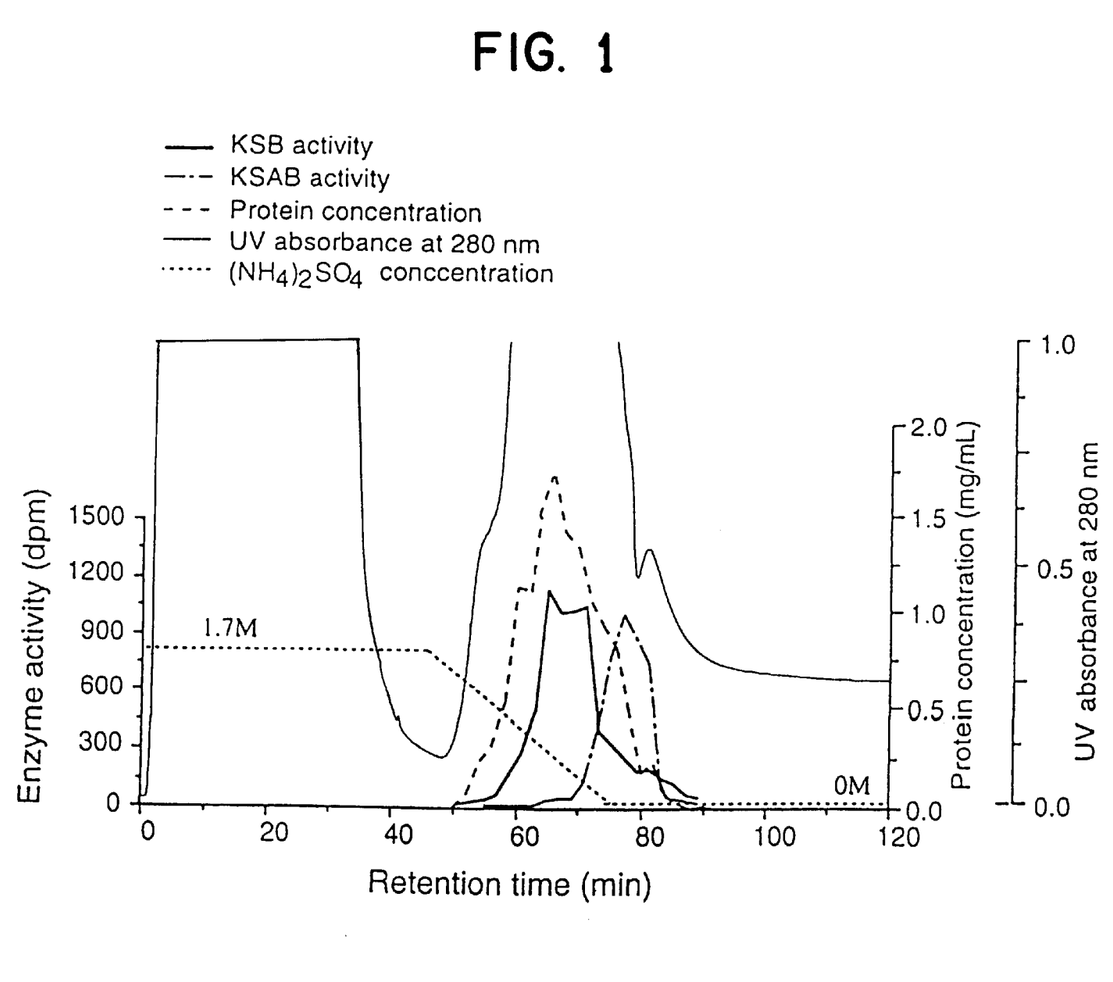
FIG. 1 is a chronatogram profile of the ent-kaurene synthase B of the present invention applied to hydrophobic interaction chromatography.

The crude enzyme prepared from immature seeds was first purified by a hydrophobic interaction chromatography in order to remove metal ions and GAs, and to concentrate the enzyme. The majority of the KSB activity was eluted at an $(NH_4)_2SO_4$ concentration of 0.6–0.1 M, whereas the majority of the KSAB activity was eluted after the $(NH_4)_2SO_4$ gradient was complete (FIG. 1). Fractions corresponding to an $(NH_4)_2SO_4$ concentration of 0.6–0.1 M were collected as the butyl-purified KSB preparation, although this preparation contained some KSA activity.

The butyl-purified KSB preparation was purified further by DEAE ion exchange chromatography with a NaCl gradient. Both KSA and KSB co-eluted at fractions corresponding to 240–360 mM NaCl. Separation of KSA and KSB was not achieved by DEAE chromatography but the specific activity of KSB was increased (Table 1). These fractions were collected and were further purified by high performance hydrophobic interaction chromatography using a Phenyl-5PW column. The majority of KSB activity eluted at $(NH_4)_2SO_4$ concentrations of 0.5–0.2 M, and KSAB activity eluted later.

Figure 2:
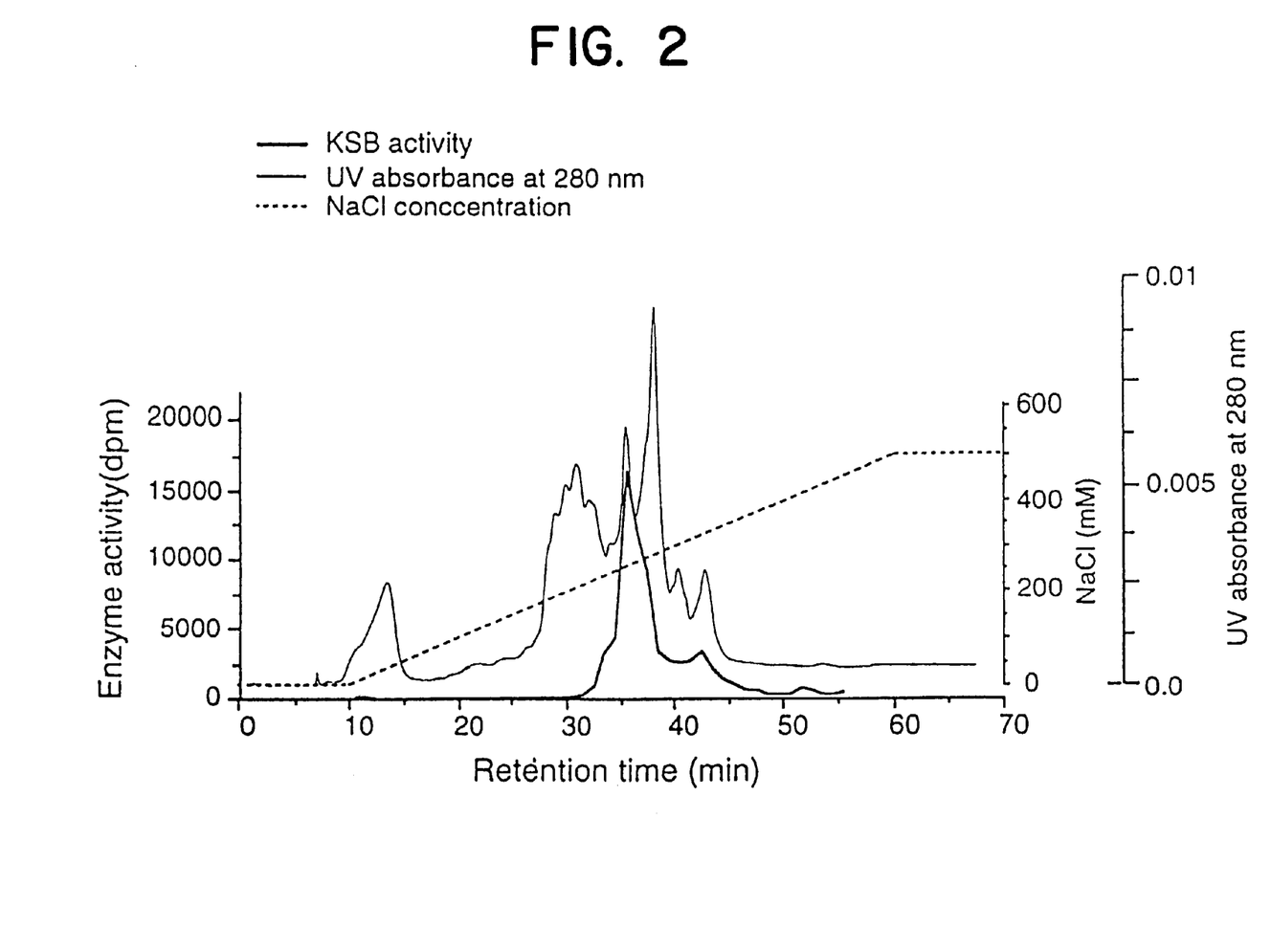
FIG. 2 is a chromatogram profile of the ent-kaurene synthase B of the present invention purified by a DEAE column.
Figure 3:
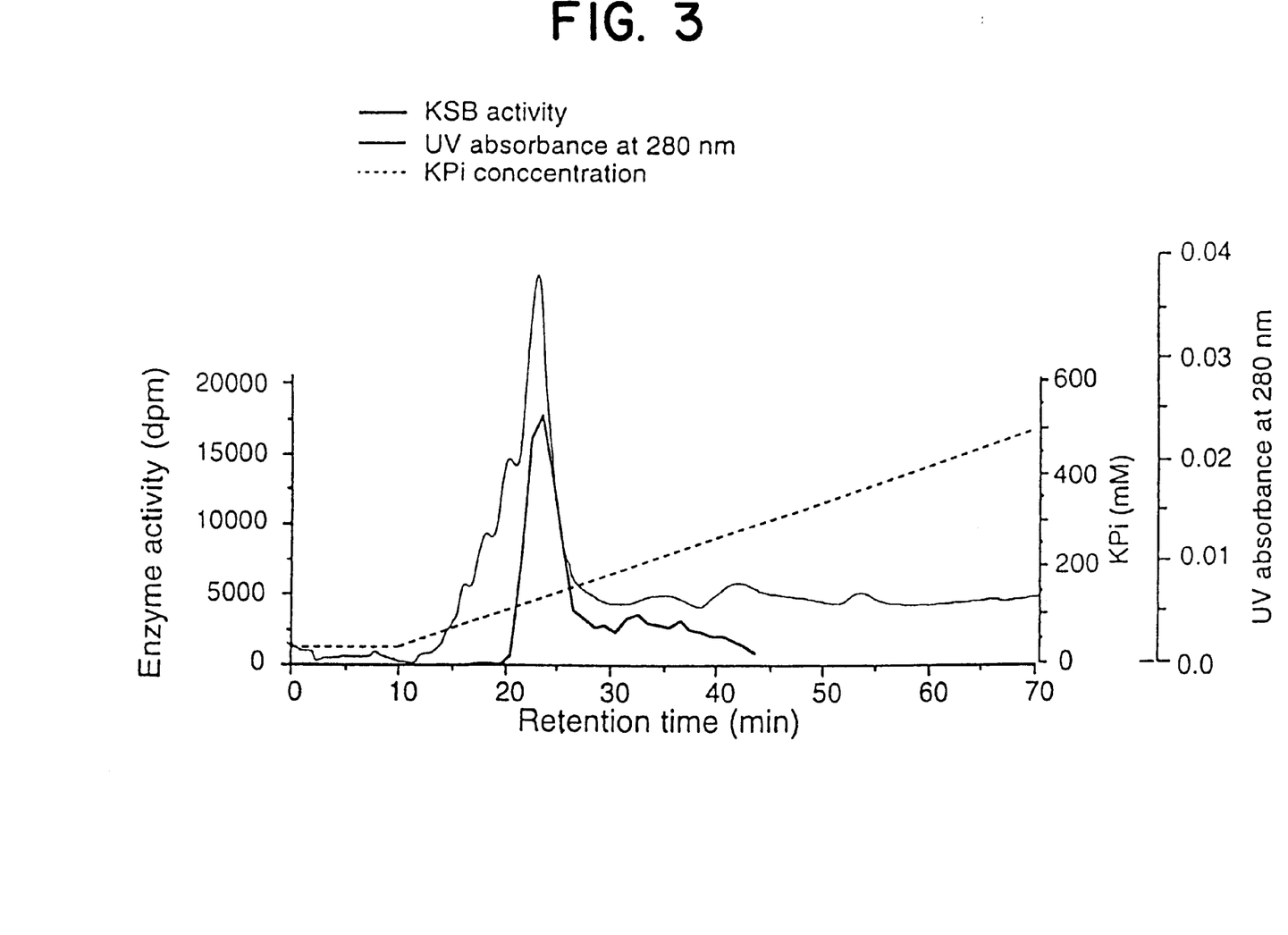
FIG. 3 is a chromatogram of an ent-kaurene synthase B of the present invention purified by a hydroxyapatite column.

About 40% of the phenyl-purified enzyme preparation was further purified on the same DEAE column. The main peak of KSB activity was detected in fractions of 250–280 mM NaCl (FIG. 2), which were collected as the second DEAE-purified enzyme preparation. This enzyme preparation contained four major proteins by SDS-PAGE, and was further purified on a hydroxyapatite column. The KSB activity was eluted at phosphate concentrations of 90–140 mM, and the peak shape of KSB activity was corresponded with that of UV-absorbance at 280 nm (FIG. 3). The purest KSB preparation did not show KSAB activity suggesting that KSA was not present in the preparation. ent-Kaurene synthase B was purified 291-fold from endosperm of Cucurbita maxima L. (Table 1) and 70 µg of purified enzyme was obtained.

TABLE 1

| Enzyme preparation | Total protein (mg) | Total activity (units) | Yield (%) | Specific activity (units/mg) | Purification (fold) |
|---|---|---|---|---|---|
| Crude enzyme | 530 | 17,500 | 100 | 33.0 | 1 |
| Butyl-purified | 168 | 11,000 | 63.8 | 65.4 | 1.98 |
| 1st DEAE-purified | 13.9 | 5,170 | 29.6 | 372 | 11.3 |
| Phenyl-purified | 4.43 | 3,340 | 19.2 | 754 | 22.8 |
| 2nd DEAE-purified | 0.407 | 2,820 | 16.2 | 6,930 | 210 |
| HA-purified | 0.070 | 673 | 3.87 | 9,610 | 291 |

(B) SDS-PAGE Analysis and Molecular Mass Estimation

The hydroxyapatite-purified enzyme preparation showed a major band at apparent molecular mass of 81 kD. The amount of protein corresponding to the 81 kD band estimated by SDS-PAGE in each fraction of the second DEAE chromatography correlated with KSB activity. To determine the molecular mass of KSB by means of gel permeation HPLC, we used a TSK G3000 SWx1 column. On this column, the elution profile of KSB was broad but centered on retention time of 23.5 min, which corresponds to an apparent molecular mass of approximately 90 kD.

(C) Properties of KSB

The properties of KSB were examined with the phenyl-purified enzyme preparation. The optimal pH for KSB was 6.8–7.5 in 50 mM KPi buffer. The $K_m$ value for [15-$^3$H]CPP was 0.35 µM. In the presence of 5 mM $Mg^{2+}$ KSB could convert CPP to ent-kaurene, but was not active without exogenous cations. Since EDTA (1–100 mM) did not change KSB activity, the phenyl-purified enzyme preparation did not contain endogenous cations that affected KSB activity.

Figure 4:
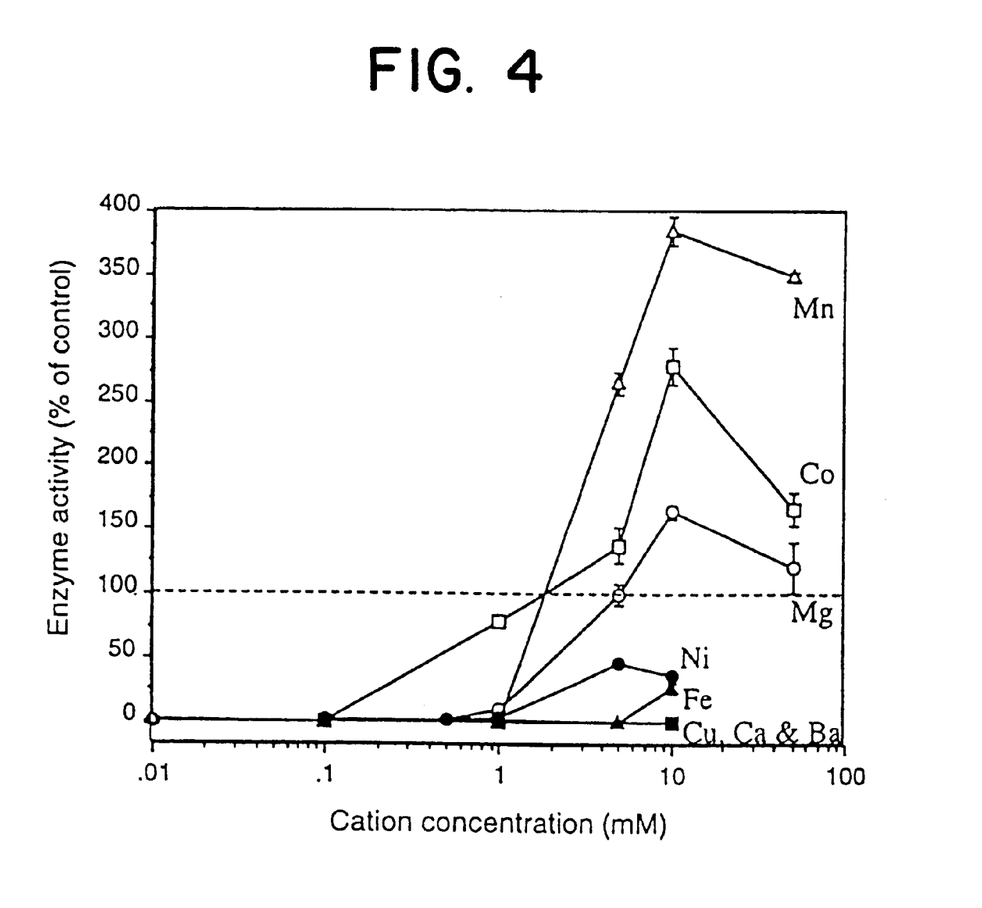
FIG. 4 shows activities of an ent-kaurene synthase B of the present invention in the presence of divalent cations.

Some divalent cations (0.1–50 mM, as chlorides) were added to the incubation mixture instead of 5 mM $Mg^{2+}$, and KSB activity was measured. As shown in FIG. 4, $Mg^{2+}$, $Co^{2+}$ and $Mn^{2+}$ promoted KSB activity and their optimal concentrations were around 10 mM. $Ni^{2+}$ and $Fe^{2+}$ weakly promoted KSB activity, while $Cu^{2+}$, $Ca^{2+}$ and $Ba^{2+}$ showed no effects. When $Cu^{2+}$, $Ca^{2+}$ and $Ba^{2+}$ were added to the incubation mixture in combination with 5 mM $Mg^{2+}$, all three inhibited KSB activity promoted by $Mg^{2+}$. In particular $Cu^{2+}$ completely inhibited the conversion promoted by 5 mM $Mg^{2+}$ at concentrations above 0.5 mM.

(D) Peptide Sequence Analysis

The N-terminal peptide sequence of the 81 kD protein from SDS-PAGE was analyzed and the N-terminus of the protein was found to be blocked. The 81 kD protein band was cut out from the polyacrylamide gel and treated with a lysyl endopeptidase, Acromobacter protease I (Masaki, T., et al., Biochem. Biophys. Acta, 660, pp.44–50, 1981). The resulting peptides were separated by reverse-phase HPLC and the sequences of the major peptides analyzed (Kawasaki, H., et al., Anal. Biochem., 191, pp.332–336, 1990). Sequences and approximate amounts of the peptides recovered are (1) ASQIITHPDESVLENINSWT (SEQ ID No: 4)(74 pmol), (2) EAEWSTNK (corresponding to Glu-Ala-Glu-Trp-Ser-Thr-Asn-Lys shown as SEQ ID No. 5) (45 pmol), (3) RAMESYSGDIVRISK (corresponding to Arg-Ala-Met-Glu-Ser-Tyr-Ser-Gly-Asp-Ile-Val-Arg-Ile-Ser-Lys shown as SEQ ID No. 6) (37 pmol), (4) HGLSSDSVW (corresponding to His-Gly-Leu-Ser-Ser-Asp-Ser-Val-Trp shown as SEQ ID No. 7) (24 pmol), (5) LQDWSMVM-QYQRK (corresponding to Leu-Gln-Asp-Trp-Ser-Met-Val-Met-Gln-Tyr-Gln-Arg-Lys shown as SEQ ID No. 8) (17 pmol).

(E) Western Blot Analysis and Immunoprecipitation

Western blot analysis showed that the polyclonal antibody raised against the synthetic peptide ASQIITHPDESVLEN-INSWT (SEQ ID No: 4), combined to keyhole limpet hemocyanin, selectively recognized the 81 kD protein in each fraction from the 2nd DEAE-chromatography, and the pattern showed a good correlation with the patterns of KSB activity and CBB staining. In an immunoprecipitation experiment using the phenyl-purified enzyme and the polyclonal antibody, the 81 kD protein was detected in the supernatant fraction and not in the precipitate regardless of the amount of antibody used.

Example 2

Cloning of Ent-kaurene Synthase Gene (A) Isolation of the KSB CDNA Clone

From the peptide sequences ([1] ASQIITHPD ESVLEN-INSWT (SEQ ID No: 4), [2] EAEWSTNK (SEQ ID No: 5), [3] RAMESYSGDIVRISK (SEQ ID No: 6), [4] HGLSS-DSVW (SEQ ID No: 7), [5] LQDWSMVMQYQRK) (SEQ ID No: 8), degenerated oligonucleotides were synthesized for PCR primers in both sense and antisense directions. Using these synthetic oligonucleotides as primers, (RT)-PCR was tried to amp lify cDNA fragments from poly(A)$^+$ RNA prepared from immature cotyledons of Cucurbita maxima.

As the result, a 472-bp CDNA fragment was amplified when a combination of the forward primer designed from the underlined part of the sequence [5] and the reverse primer from the underlined sequence in [1] was used as a primer set. The amino acid sequence showed relatively high homology with KSA of Arabidopsis (39% identity, 66% similarity). Because the amino acid sequence of this region of putative maize KSA (Bensen, R. J. et al., Plant Cell, 7, pp.75–84, 1995) has much higher homology with Arabidopsis KSA, it was suggested that the PCR amplified fragment was not a part of KSA, but th at of one of other terpene cyclases.

Using the PCR-amplified fragment as a probe, RNA blot analysis was performed against poly(A)$^+$RNA prepared from the same material to d etect a 2.7-kb transcript, a possible size compared to the estimated size of the purified protein (81 kD). Considering these results together with the fact that the final purified enzyme fraction (the hydroxyapatite purified fraction as described above) used for sequencing did not contain KSA activity but had KSB activity, it is strongly suggested that the 472-bp PCR-amplified fragment encodes a part of KSB cDNA.

To obtain a full-length KSB cDNA clone, a cDNA library consisting of 1.2 million independent clones was constructed from poly(A)$^+$ RNA prepared from immature cotyledons of Cucurbita maxima using λ ZAP II as a vector. After the amplification of the library, 5×10$^5$ clones were screened to isolate 9 independent clones after 3 rounds of purifications. After the subcloning into pBluescriptSK(-), the size of the insert cDNA was determined to select 2 clones, pKB3 and pKB16 for further studies. Both of the clones contained 2.4-kb insert and showed same restriction enzyme maps.

Comparison of the size of the cDNA insert and that of the transcript detected in Northern blot (2.7 kb) implied that the inserts of pKB3 and pKB16 are 5'-truncated DNAs. The method of rapid amplification of cDNA ends was used for the isolation of the 5'-region of pKB16, and a 0.6-kb cDNA fragment containing an additional 263 bp in 5'-region was isolated, which was fused to pKB16 by use of PstI site locating at nucleotide 722. The resulting plasmid clone containing the fused cDNA was named pKB20.

(B) Sequencing Analysis of pKB20 pKB20 contains a cDNA insert consisting of 2658 nucleotides, which contains the identical sequence (801 to 1269) to the PCR amplified fragment which was used as a probe. The nucleotide sequence of the full length cDNA is given in SEQ ID NO:2 of the sequence listing. The KSB code region of the cDNA and the amin o acid sequence of the corresponding KSB are given in SEQ ID NO:3 of the sequence listing. The amino acid sequence of KSB is shown in SEQ ID NO:1 of the sequence listing according to the IUPAC single character coding. The ATG codon at the position of 138 to 140 is most likely the starting codon for KSB protein, which is followed by a long ORF of 2367 nucleotides and polyadenylation signal sequence (AATAAA) at the position of 103 to 109 nucleotides downstream from the translational stop codon.

The ORF consists of 789 amino acids, where all the peptide sequences obtained from the protease-digested purified protein are detected, although there was a change of amino acid in (5) LQDWSMVMQYQRK (SEQ ID No: 8) to LQDWDMVMQYQRK (corresponding to Leu-Gln-Asp-Trp-Asp-Met-Val-Met-Gln-Tyr-Gln-Arg-Lys shown as SEQ ID No. 9). The first 50 N-terminal amino acid sequence is rich in serine (18%) and threonine (12%) and the estimated pI of this region is 9.8, which are common characters of transit peptides targeting chloroplasts (ceegstra, et al., Annu. Rev. Plant Physiol. Mol. Biol., 40, 471–501, 1989).

As shown in above example 1, the polyclonal antibody raised against the synthetic oligopeptide, [1] ASQIITHP-DESVLENINSWT (SEQ ID No: 4), combined to a carrier protein did not recognize the native KSB protein, although it recognized a 81 kD protein on SDS-PAGE. From the results, it was predicted that the peptide sequence located not on the surface, but in the core part of the properly folded protein, so that the antibody could recognize only the denatured protein. In the sequence of above, the peptide sequence used for the production of the antibody is found in just the middle of the sequence (nucleotide 1244 to 1304), not in the N-terminus nor C-terminus region, which are supporting the experimental results of Example 1.

(C) Expression of KB20 Protein in *Escherichia coli*

To confirm whether pKB20 encodes KSB, the protein encoded by the cloned cDNA was over-expressed as a fusion protein with maltose binding protein (Guan, et al., Gene, 67, 21–30, 1987) in *Escherichia coli* to analyze the enzyme activity of the expressed protein. Plasmid PMAL-KB containing a fragment (tac promoter sequence-malE-KSB) for the expression of the fusion protein (MBP-KB) and the control plasmid PMAL (42 kD for MBD expression) containing tac-promoter sequence-malE fragment were prepared.

In this system, the expression of the fusion protein is under the regulation of tac promoter, which is induced by the addition of isopropyl-b-D-thiogalactopyranoside (IPTG). On an SDS-PAGE followed by Coomassie blue staining, a band of an expected size (131 kD) of the fusion protein (MBP-KB) was detected in total protein extract of *E. coli* which carries pMALKB after IPTG induction. Immunoblot analysis was performed to confirm whether the IPTG-induced protein is recognized by the anybody against the synthetic peptide. Immuno-reactivity was detected on the band corresponding to the IPTG-induced protein, and additional bands of smaller size were also detected, which seemed to be the degradation products of the KB20 protein. However, no immuno-staining was observed in the protein of *E. coli* producing MBP only, regardless of the addition of IPTG.

(D) Functional Analysis of KB20 Protein

To analyze the enzyme activity of MBP-KB, soluble proteins were prepared from *E. coli* producing the fusion protein. But only a trace amount of the fusion protein was found in the soluble fraction, suggesting that the most of the fusion protein formed an inclusion body, when the *E. coli* was cultured under normal conditions. Bishai et al. (Bishai, et al., J. Bact. 169, pp.5140–5151, 1987) reported that when *E. coli* is cultured at a low temperature after the induction by IPTG, the ratio of the over-expressed fusion protein in a fraction of soluble proteins increased. In the case of MBP-KB, at 20° C., the ratio of MBP-KB protein in soluble fraction raised to about 10 folds compared to *E. coli* cultured at 37° C. The temperature fits a physiological condition of the plant which is the origin of the enzyme, thus is seemed to help the stability of the enzyme to culture *E. coli* at a low temperature (20° C. ).

The conversion to ent-kaurene was analyzed using the soluble protein extract of *E. coli* grown at 20° C. after the addition of IPTG, according to the KSB enzyme assay as the above Example 1 and adding [$^3$H]CPP to the extracts of *E. coli* which carries PMALKB or pMAL. After the incubation of [$^3$H]CPP with the *E. coli* extracts in the presence of Mg$^{2+}$ (cofactor for KSB of pumpkin) and uniconazole (an inhibitor of ent-kaurene oxidation), the reaction mixture was extracted with n-hexane followed by fractionation on silica-gel thin-layer chromatography (TLC) to isolate LP (low polarity) fraction, where ent-kaurene is fractionated.

KSB activity was tentatively defined as the radioactivity (dpm) of the "LP fraction". The extract of *E. coli* producing MBP-KB20 showed significant KSB activities, although that of the bacteria cells expressing only MBP had no activities. It was analyzed on OSD-HPLC to confirm whether the radioactivity in "LP fraction" on TLC corresponds to ent-kaurene. The retention time of the major peak in LP fraction of the *E. coli* extract was identical to that of the original pumpkin enzyme preparation, besides, those of them are identical to retention time of authentic [$^{14}$C]ent-kaurene. It was also proved that the radioactivity in LP fraction of the *E. coli* extracts were mostly derived from the major peak (95%) identical to ent-kaurene fraction. Thus, it was indicated that the extract of *E. coli* producing MBP-KB had enzyme activity to convert CPP to ent-kaurene.

According to the results of Northern blotting, KSB transcripts were detected in all of the tested tissues and this fact indicates that the KSB could be expressed not only in immature seeds but in vegetative tissues. On the other hand, a message of 20-oxidase of pumpkin is detected only in immature seeds in contrast to KSB (Lange, T., et al., Proc. Natl. Acad. Sci. USA, 91, pp.8552–8556, 1994). The expression level of KSB is relatively high in young tissues and the transcripts were detected most abundantly in growing cotyledon on growth of immature seeds.

(E) Sequence Comparison with other Terpene Cyclases

The deduced amino acid sequence of KB20 and sequences of other terpene cyclases, including KSAs, was analyzed with comparison to each other. KB20 sequence shared homology with tobacco sesquiterpene cyclase (Facchini, P. J., Proc. Natl. Acad. Sci. USA, 89, pp.11088–11092, 1992), limonene synthase (Colby, S. M., J. Biol. Chem., 268, pp.23016–23024, 1993), caster bean casbene synthase (Colby, S. M., J. Biol. Chem., 268, pp.23016–23024, 1993) and in particular, Arabidopsis KSA (Sun T. P. and Kamiya, Y., Plant Cell, 6, pp.1509–1518, 1994).

Around the center part of the sequences (amino acid 337 to 600) are well conserved in all the terpene cyclases analyzed (Sun T. P. and Kamiya, Y., Plant Cell, 6, pp.1509–1518, 1994). Arabidopsis KSA and KSB20 shared the identical amino acids in the first part of the sequences (amino acid 114 to 230, 34.8% identity), although common amino acid between the KSA and the KSB are hardly observed in the last part of the sequences (amino acid 601 to the terminus). However, KSB and cyclases other than KSA shared some conserved amino acid in the region of amino acid 603 to 631.

What is claimed is:

1. An isolated DNA encoding a polypeptide comprising the amino acid sequence as set forth in SEQ ID NO: 1.

2. The isolated DNA according to claim 1 comprising nucleotide Nos. 138–2507 of the nucleic acid sequence as set forth in SEQ ID NO: 3.

3. An isolated anti-sense DNA of an ent-kaurene B synthase gene comprising a DNA sequence fully complementary to nucleotide Nos. 138–2507 of the nucleic acid sequence as set forth in SEQ ID NO: 3.

4. A recombinant vector comprising the DNA according to claim 1.

5. A transformant comprising the recombinant vector according to claim 4.

6. A recombinant vector comprising the DNA according to claim 2.

7. A transformant comprising the recombinant vector according to claim 6.

8. A recombinant vector comprising the DNA according to claim 3.

9. A transformant comprising the recombinant vector according to claim 8.

10. An isolated DNA comprising the DNA of claim 1, and encoding a protein having a catalytic activity of converting copalyl pyrophosphate to ent-kaurene.

11. An isolated DNA comprising the DNA of claim 2, and encoding a protein having a catalytic activity of converting copalyl pyrophosphate to ent-kaurene.

12. An isolated DNA encoding a polypeptide comprising a fragment of the amino acid sequence set forth in SEQ ID NO:1 which has a catalytic activity of converting copalyl pyrophosphate to ent-kaurene.

13. An isolated DNA encoding a protein comprising a fragment obtained from the polypeptide of claim 1, said fragment being an active domain catalyzing the conversion of copalyl pyrophosphate to ent-kaurene.

* * * * *